United States Patent
Prestipino

(10) Patent No.: US 9,504,534 B2
(45) Date of Patent: Nov. 29, 2016

(54) APPARATUSES AND METHODS FOR IMPLANTING DENTAL IMPLANTS

(71) Applicant: Vincent Prestipino, North Bethesda, MD (US)

(72) Inventor: Vincent Prestipino, North Bethesda, MD (US)

(*) Notice: Subject to any disclaimer, the term of this patent is extended or adjusted under 35 U.S.C. 154(b) by 0 days.

(21) Appl. No.: 14/733,367

(22) Filed: Jun. 8, 2015

(65) Prior Publication Data
US 2016/0038254 A1 Feb. 11, 2016

Related U.S. Application Data

(60) Provisional application No. 62/035,087, filed on Aug. 8, 2014.

(51) Int. Cl.
*A61C 8/00* (2006.01)
*A61C 1/08* (2006.01)

(52) U.S. Cl.
CPC ............. *A61C 1/084* (2013.01); *A61C 8/0022* (2013.01); *A61C 8/0089* (2013.01); *A61C 8/0087* (2013.01)

(58) Field of Classification Search
CPC .............................. A61C 1/084; A61C 8/0089
See application file for complete search history.

(56) References Cited

U.S. PATENT DOCUMENTS

| | | | |
|---|---|---|---|
| 8,105,081 B2 * | 1/2012 | Bavar | A61C 1/084 433/215 |
| 8,414,296 B2 | 4/2013 | Berckmans, III et al. | |
| 8,967,999 B2 | 3/2015 | Suttin et al. | |
| 2002/0142266 A1 | 10/2002 | Rogers et al. | |
| 2005/0170311 A1 * | 8/2005 | Tardieu | A61C 8/0089 433/76 |
| 2006/0008763 A1 * | 1/2006 | Brajnovic | A61C 8/0089 433/76 |
| 2006/0008770 A1 * | 1/2006 | Brajnovic | A61C 8/0089 433/141 |
| 2007/0111163 A1 | 5/2007 | Powell et al. | |
| 2009/0239197 A1 * | 9/2009 | Brajnovic | A61C 1/084 433/174 |
| 2010/0062389 A1 * | 3/2010 | Drews | A61B 17/176 433/75 |
| 2010/0209868 A1 * | 8/2010 | De Clerck | A61C 1/084 433/72 |
| 2010/0297574 A1 * | 11/2010 | Llop | A61C 1/084 433/75 |
| 2011/0306009 A1 | 12/2011 | Suttin et al. | |
| 2012/0191103 A1 | 7/2012 | Jorneus et al. | |
| 2013/0224685 A1 | 8/2013 | Cheng et al. | |
| 2014/0051038 A1 | 2/2014 | Berckmans, III et al. | |

* cited by examiner

*Primary Examiner* — Ralph Lewis
(74) *Attorney, Agent, or Firm* — Haynes and Boone, LLP

(57) ABSTRACT

The invention includes apparatuses and methods for implanting dental implants in a patient's mouth that ensure that the implants are in the proper rotational position and depth. In one aspect, the invention includes a surgical guide with a guide tube having an indexing mechanism that mates with a corresponding indexing mechanism on a flange of an implant mount when the mount is used to screw an implant into a patient's mouth. This mating signals that the dental implant is in the proper rotational position and depth.

20 Claims, 7 Drawing Sheets

APPARATUSES AND METHODS FOR IMPLANTING DENTAL IMPLANTS

CROSS-REFERENCE TO RELATED APPLICATION

This application claims the benefit of U.S. Provisional Application No. 62/035,087, filed on Aug. 8, 2014, the contents of which are incorporated herein by reference.

FIELD OF THE INVENTION

This invention pertains to the field of dental implants.

BACKGROUND OF THE INVENTION

Dental implants are implanted into the jawbone of a patient that has lost some or all of his or her teeth in that jawbone. In a common procedure for implanting dental implants, CT (CBCT-DICOM files) data and optical scan (STL files-STereoLithography) data regarding the precise location of the teeth, gums and bone in the patient's mouth are collected at some point prior to the surgery where an implant surgeon or restorative dentist implants the dental implants into the patient's mouth. These data are used with dental implant case planning software to plan the surgery during which dental implants will be implanted. This planning includes the fabrication of a surgical guide to be placed in the patient's mouth during the surgery. The surgical guide is often horseshoe-shaped (like the shape of one arch of teeth), and made of a thermoplastic or non-thermoplastic resinous base. This planning also includes a surgical protocol for the preparation of each site in the patient's jawbone where a dental implant will be implanted. The protocol provides detailed information regarding the preparation of each implant site, including information about the proper sequence of drill bits to be used at each site, and the selection of tube adapter sleeves (described further below) to be used at each site. The surgical guide and protocol are often prepared by a dental implant manufacturer, a supplier of dental implant case planning software, or a dental laboratory.

In use, the surgical guide is removably affixed in the patient's mouth using techniques known to those skilled in the art. The surgical guide rests on the patient's gums and intact teeth and has openings showing the precise locations where each dental implant is to be implanted. Each opening is defined by a guide tube, which is a ring that is often made of titanium. Following the protocol, for each implant site, the surgeon or dentist attaches a first tube adapter sleeve (having a specific size and orientation) to the guide tube of the surgical guide, and then places a drill with a first drill bit (having a specific size) through the first tube adapter sleeve and drills a hole in the jawbone having a size and orientation determined by the surgical guide, the first tube adapter sleeve and the first drill bit. This is the first step in the drilling of the hole in the jawbone into which the dental implant will ultimately be implanted. The surgeon or dentist then removes the drill and first drill bit, and attaches a second tube adapter sleeve (having a slightly larger size than the first tube adapter sleeve) to the opening in the surgical guide, and uses a second drill bit, slightly larger than the first drill bit, to make the hole in the patient's jawbone slightly larger. The process of using progressively larger tube adapter sleeves and drill bits continues until the hole in the patient's jawbone has the size called for by the surgical protocol. In a typical process, the surgeon or dentist may start with a 2 mm drill bit, and then progress to a 3 mm and then a 4 mm drill bit, with the guide tube having a diameter of 5 mm.

At this point, the hole in the patient's jawbone is ready to have the dental implant implanted into it. The dental implant is then often attached to an implant mount (or holder). The implant mount protrudes up from the patient's jawbone when a dental implant is being inserted into the jawbone, and provides a member to which the surgeon or dentist can attach a hand-piece, a drill or ratchet device when screwing the implant into the jawbone. The implant mount has a lower shaft that has the same diameter as the opening in the surgical guide defined by the guide tube. The dental implant (attached to the implant mount) is then inserted through the opening in the surgical guide defined by the guide tube, and screwed into the hole in the patient's jawbone that has been created through use of the drill bits and tube adapter sleeves described above. The implant mount has a flange at the top of the shaft that controls the depth that the dental implant is screwed into the jawbone. The flange is wider than the opening in the surgical guide defined by the guide tube. The implant mount is screwed into the jawbone until the flange comes into contact with the top of the guide tube portion of the surgical guide, which signals that the implant mount has been screwed in to the proper depth.

The top of the dental implant often has an interlocking mechanism (such as an internal hexagon-shaped opening) that must be rotated to a proper rotational position (e.g., with the flat sides of the internal hexagon-shaped opening in a specific rotational position). One technique for trying to ensure that the implant ends up in the proper rotational position is to place vertical lines or notches on both the implant mount and the surgical guide, which are lined up with one another when the implant mount is in the proper rotational position. See, e.g., U.S. Pat. No. 8,414,296 B2 at column 9, lines 31-47. However, this technique has several limitations. First, a visual inspection of both the implant mount and the surgical guide is necessary, which may be difficult, especially when the dental implant is to be implanted in the posterior of the mouth, and which depends heavily on operator evaluation and experience to avoid over-rotating the implants. Second, the implant mount may be over-rotated in an effort to get the lines to vertical lines or notches to line up, which may cause compression, warping and/or fracture of the surgical guide, and thus inaccurate placement in any of the three axes of both the implant attached to the implant mount that was over-rotated, and any additional implants to be implanted with that surgical guide. When implants are not rotated to their proper rotational position, much additional time and effort is needed to fabricate a prosthesis (whether it be a single prosthetic tooth or a prosthesis including a full arch of prosthetic teeth) to be attached to the dental implants. Thus, there exists a need in the art for an improved technique for ensuring that dental implants are rotated to their proper rotational position when they are being screwed into the jawbone.

One example of a conventional procedure for using a surgical guide to first drill a hole in a patient's jawbone and then implant a dental implant into that hole is described in Nobel Biocare's NobelGuide™: Concept manual for guided surgery.

SUMMARY OF THE INVENTION

The present invention addresses the drawbacks of current techniques for ensuring that dental implants are rotated to their proper rotational position when they are being screwed into the jawbone. In accordance with one aspect of the present invention, an interlocking mechanism (such as clutch teeth) is included on the proximal surface of the flange of the implant mount, and a corresponding interlocking mechanism is included on the distal surface of the guide tube that defines the opening in the surgical guide. When the implant mount is used to screw the dental implant into the jawbone, the interlocking mechanism on the proximal surface of the flange of the implant mount mates with the interlocking mechanism on the distal surface of the guide tube. The interlocking mechanism on the guide tube is oriented so that, when the interlocking mechanism on the proximal surface of the flange mates with it, the dental implant will be rotated to the proper rotational position. The surgeon or dentist need not make a visual inspection of the implant mount and the surgical guide to be sure that the dental implant has been rotated to the proper rotational position. Rather, the tactile feedback provided when the interlocking mechanism on the proximal surface of the flange mates with the interlocking mechanism on the distal surface of the guide tube will inform the surgeon or dentist that the dental implant is in the proper rotational position. Moreover, the operator skill and experience needed to rotate the dental implant to the proper rotational position is minimized. Finally, the possibility of over-rotating the implant mounts is reduced, as it is difficult to rotate the implant mounts past the point where the interlocking mechanism on the proximal surface of the flange mates with the interlocking mechanism on the distal surface of the guide tube.

BRIEF DESCRIPTION OF THE DRAWINGS

Specific examples have been chosen for purposes of illustration and description, and are shown in the accompanying drawings, forming a part of the specification.

DETAILED DESCRIPTION OF THE INVENTION

In one aspect of the present invention, a specially-designed surgical guide and specially-designed implant mount are used in implanting one or more dental implants into the jawbone of a patient. To illustrate the invention, it is helpful to illustrate the design of a conventional surgical guide and a conventional implant mount, and to compare them to the surgical guide and implant mount of the invention.

As used herein, the term "proximal" refers to a portion of a surgical guide, guide tube, implant mount or dental implant located closer, than a "distal" portion of the same device, to the jawbone when these devices are placed or applied in the patient's mouth. The term "distal" refers to a portion of a surgical guide, guide tube, implant mount or dental implant located further away, relative to the corresponding "proximal" portion, from the jawbone when these devices are placed or applied in the mouth. For instance, the proximal surface of a surgical guide is the surface of the surgical guide that faces the gums or teeth of the patient when the surgical guide is placed in the mouth for dental implantation. In contrast, the distal surface of the surgical guide is the surface of the surgical guide opposite to the proximal surface. In other words, the distal surface of the surgical guide is the surface that faces away from the gums or teeth when the surgical guide is placed in the mouth for the dental implantation. Similarly, the proximal shaft of an implant mount is closer to the jawbone than the distal shaft of the implant mount when the implant mount is used to screw a dental implant into the jawbone of the patient.

Figure 1A:
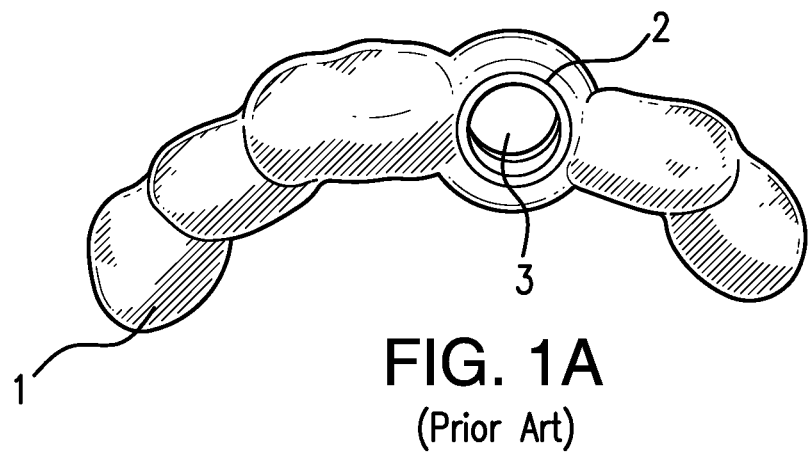
FIG. 1A illustrates a conventional surgical guide of the prior art.
Figure 1B:
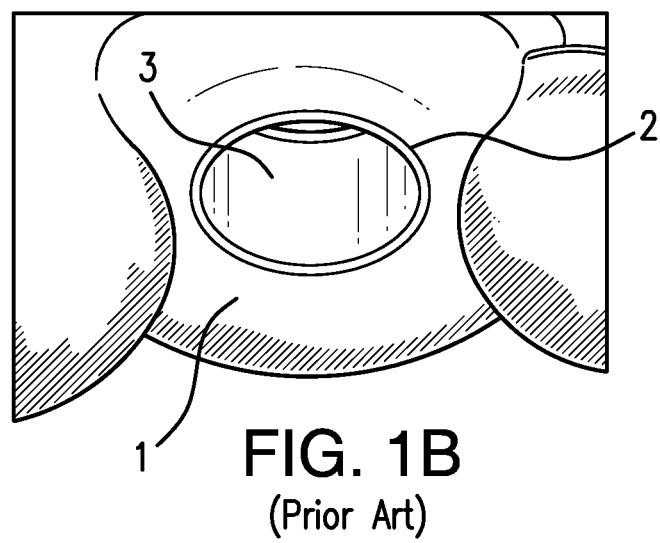
FIG. 1B is a close-up view of a guide tube and opening in a conventional surgical guide of the prior art.

Accordingly, FIG. 1A illustrates a conventional surgical guide 1 including conventional guide tube 2 with opening 3. FIG. 1B is a close-up view of a guide tube 2 and opening 3 in a conventional surgical guide 1. The surface of the distal end of the conventional guide tube 2 is flat.

Figure 1C:
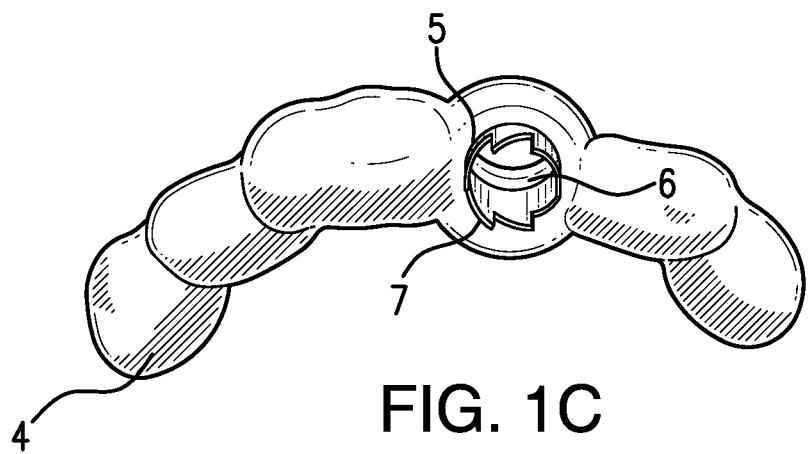
FIG. 1C illustrates a surgical guide of the present invention.
Figure 1D:
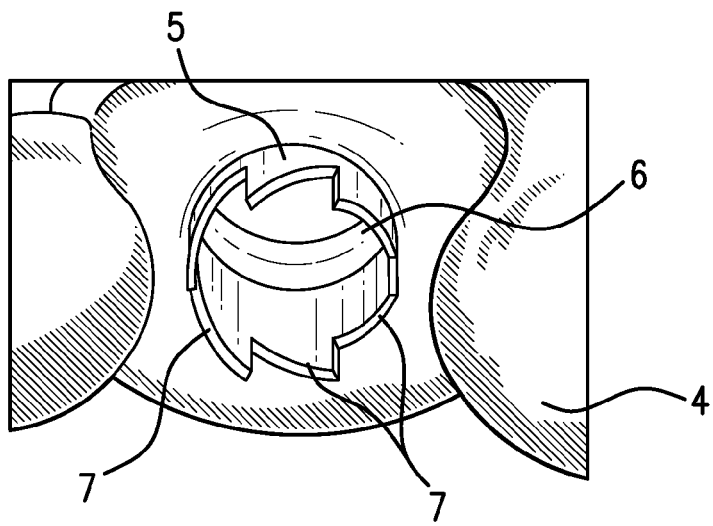
FIG. 1D is a close-up view of a guide tube and opening in a surgical guide of the present invention.

FIG. 1C illustrates one embodiment of a surgical guide 4 of the present invention, including the guide tube 5 of the present invention with opening 6. FIG. 1D is a close-up view of the guide tube 5 of the present invention and opening 6 in the surgical guide 4 of the present invention. In this embodiment, the surface of the distal end of the guide tube has clutch teeth 7 protruding from it. The surgical guide and guide tube may be fabricated from various materials known to those skilled in the art. Preferred materials for the surgical guide are thermoplastic resinous bases and non-thermoplastic resinous bases, while a preferred material for the guide tube is titanium. Various locking mechanisms known to those skilled in the art can be provided between the surgical guide and the guide tube to create a strong and stable one-piece device. For example, the outside surface of the guide tube may be hexagonal or square, and the interior surface of the opening of the surgical guide into which the guide tube fits may be hexagonal or square, with the mating of the corresponding shapes locking the guide tube in the surgical guide. The guide tube may be a complete 360° ring, or it may have an opening in its side so that it is not a complete 360° ring (e.g., it may be 240° or 300° around), with the surgical guide having a corresponding opening in its side. This latter arrangement provides easier instrument placement in the posterior of the mouth.

As noted, a surgical guide (whether it is a conventional surgical guide 1 or a surgical guide 4 of the present invention) is designed to fit on top of the patient's gums or intact teeth, and to be removably affixed in the patient's mouth using techniques known to those skilled in the art. The opening (or openings) in the surgical guide corresponds to a location (or locations) where the patient is missing a tooth (or teeth), and where a dental implant (or implants) is to be implanted.

Figure 2A:
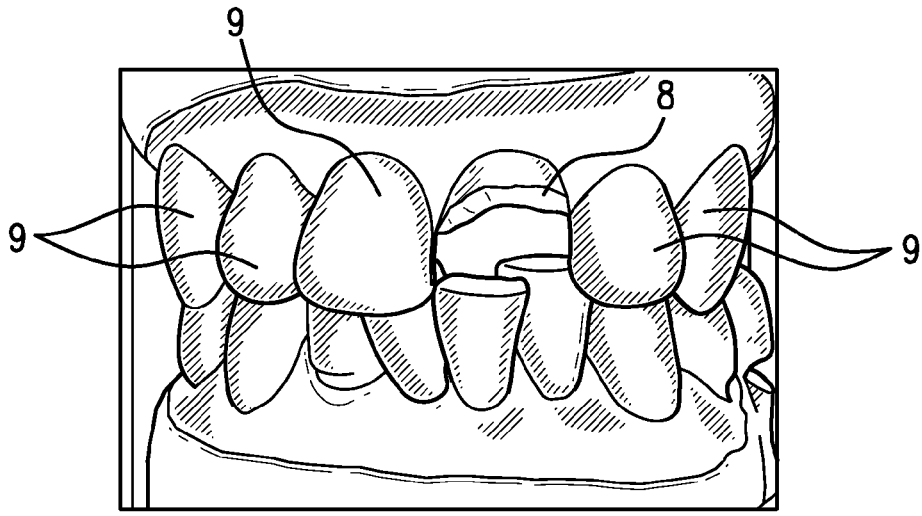
FIG. 2A illustrates a patient's mouth into which a dental implant will be implanted.
Figure 2B:
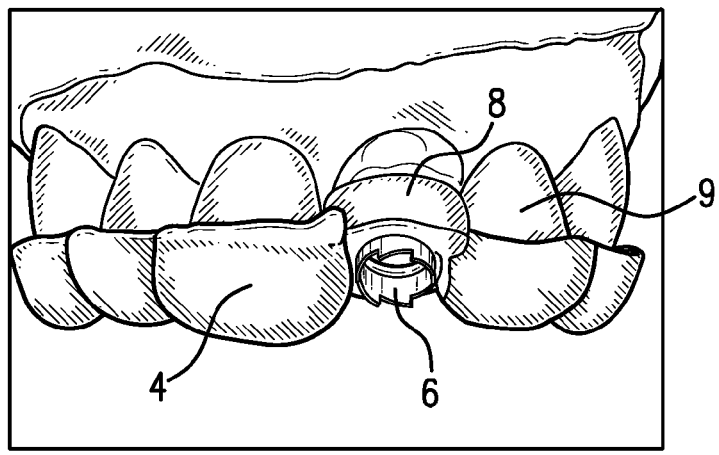
FIG. 2B illustrates a surgical guide of the present invention placed in a patient's mouth into which a dental implant will be implanted.

FIG. 2A illustrates the mouth of a patient who is to have a dental implant implanted using a surgical guide. There is a location 8 where there is a missing tooth surrounded by adjacent, intact teeth 9. FIG. 2B illustrates the mouth depicted in FIG. 2A with the surgical guide 4 now placed in the mouth. Opening 6 in the surgical guide 4 corresponds to the location 8 of the missing tooth.

Figures 3A, 3B, 3C:
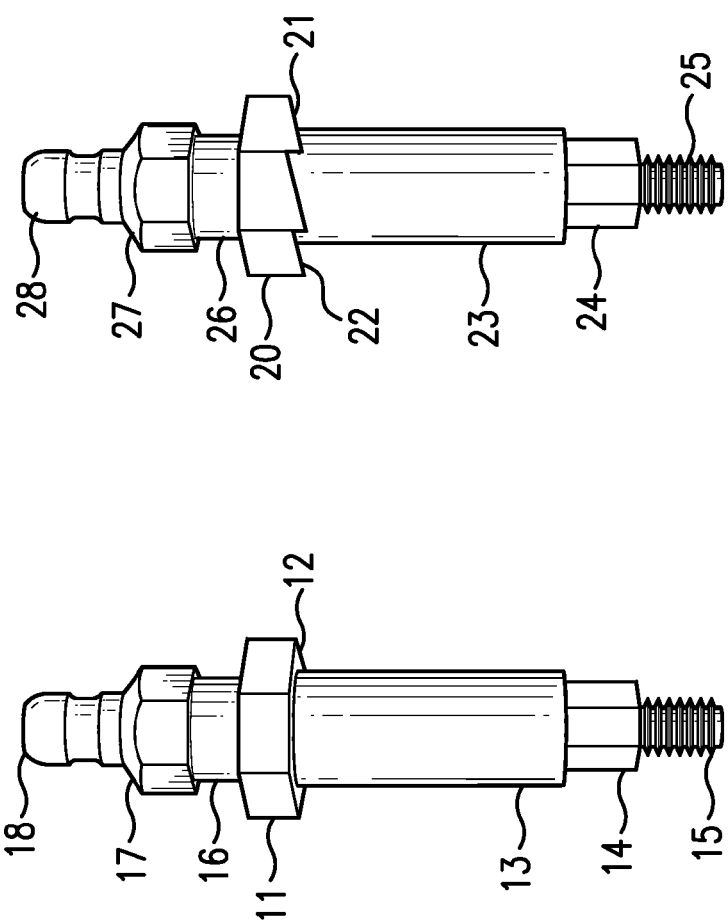
FIG. 3A illustrates a conventional implant mount of the prior art.
FIG. 3B illustrates an implant mount of the present invention.
FIG. 3C illustrates a dental implant.

As noted, an implant mount holds a dental implant while it is being implanted into a patient's mouth. FIG. 3A illustrates a conventional implant mount 10 having a conventional flange 11. Note that the proximal surface 12 of conventional flange 11 of conventional implant mount 10 is flat. Proximal to the conventional flange 10 are proximal shaft 13, proximal hexagonal member 14, and proximal threaded tip 15. Distal to the conventional flange 11 are distal shaft 16, distal hexagonal member 17 and distal tip 18.

FIG. 3B illustrates an embodiment of an implant mount 19 of the present invention having flange 20 of the present invention. In this embodiment, the flange 20 has clutch teeth 22 protruding from its proximal surface 21. As will be described below, these clutch teeth 22 mate with the clutch teeth 7 protruding from the distal surface of the guide tube 5 of the present invention. Other than the flange 20 with clutch teeth 22, the implant mount 19 of the present invention is similar to conventional implant mount 10. Proximal to the flange 20 are proximal shaft 23, proximal hexagonal member 24, and proximal threaded tip 25. Distal to the flange 20 are distal shaft 26, distal hexagonal member 27, and distal tip 28. An implant mount of the present invention may not have all of the features depicted in FIG. 3B, or may have other features, but it should at least have flange 20 with clutch teeth 22 or another similar indexing mechanism to mate with a corresponding indexing mechanism on the distal surface, inside surface or outside surface of the guide tube of the present invention.

FIG. 3C illustrates a dental implant 29. The implant has threads 30 that are designed to screw into a hole in the jawbone of a patient that has been created by the surgeon or dentist using a drill.

Figure 3D:
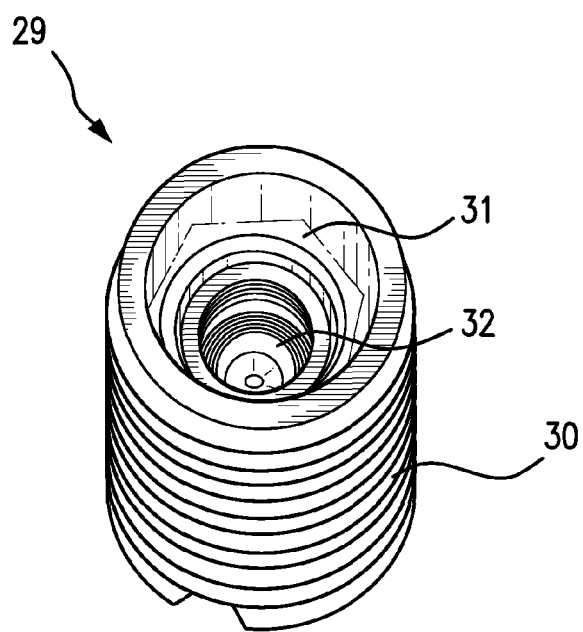
FIG. 3D is a close-up view of a dental implant.

FIG. 3D is a close-up view of the distal end of dental implant 29 with threads 30. The distal end of the dental implant 29 includes an internal hexagon-shaped opening 31 cut into the implant, with a smaller, threaded bore 32 below that opening. The distal end of the dental implant 29 is designed to mate with the proximal surface of the flange of the implant mount 19, with the proximal threaded tip 25 of the implant mount 19 screwing into the threaded bore 32 of the dental implant 29, and the proximal hexagonal member 24 of the implant mount 19 fitting into the internal hexagon-shaped opening 31 of the dental implant 29.

Figure 3E:
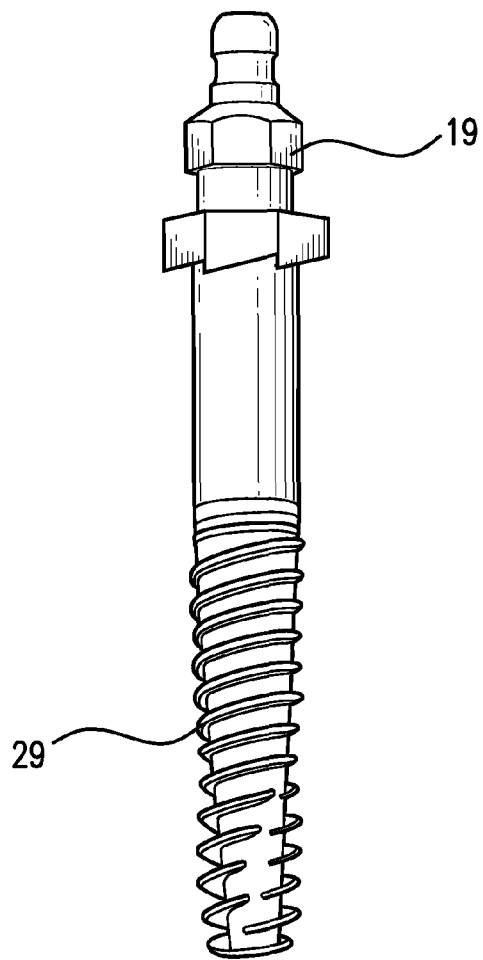
FIG. 3E illustrates an implant mount of the present invention attached to a dental implant.

FIG. 3E illustrates implant mount 19 mated with dental implant 29.

The manner in which a surgical guide and implant mount are used to implant a dental implant into the jawbone of a patient is as follows. As illustrated in FIG. 2B, the surgical guide (whether it be conventional surgical guide 1 or a surgical guide of the present invention 4) is removably affixed in the patient's mouth so that an opening in the surgical guide corresponds to the location of a missing tooth. The implant mount (whether it be conventional implant mount 10 or an implant mount 19 of the present invention) is attached to the dental implant as depicted in FIG. 3E. A hand-piece, drill or ratchet device (not shown) is then attached to the distal hexagonal member 27 and distal tip 28 of the implant mount 19 (or to the distal hexagonal member 17 and distal tip 18 of the implant mount 10). The dental implant is inserted through the opening in the surgical guide and into a hole previously drilled in the patient's jawbone, and the drill or ratchet device is then used to screw the dental implant into the patient's jawbone. Typically, a hand-piece will be used first, followed by a drill and then a ratchet device.

The diameter of the proximal shaft on the implant mount is the same as the diameter of the opening in the guide tube. Thus, the proximal shaft of the implant mount will fit through the guide tube. However, the flange on the implant mount is wider than the opening in the guide tube. Accordingly, when a dental implant is being screwed into the patient's jawbone using an implant mount, the proximal surface of the flange of the implant mount eventually comes into contact with the distal surface of the guide tube in the surgical guide, and prevents the dental implant from being screwed any more deeply into the patient's jawbone. When the proximal surface of the flange on the implant mount comes into contact with the distal surface of the guide tube of the surgical guide, that tells the surgeon or dentist that the dental implant has been screwed the proper depth into the patient's jawbone, and that no further rotating is necessary. The implant mount is then unscrewed from and/or lifted out of the dental implant, and removed from the patient's mouth, leaving the dental implant screwed into the patient's jawbone.

Figure 4A:
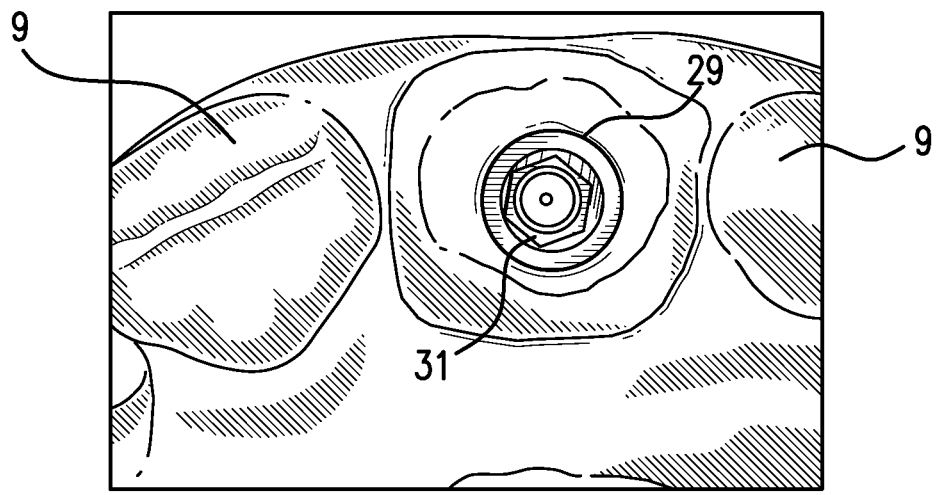
FIG. 4A illustrates a dental implant implanted into a patient's mouth.

FIG. 4A illustrates a dental implant 29 that has been implanted into a patient's jawbone. Note that the internal hexagon-shaped opening 31 of the dental implant 29 has a certain rotational position with respect to the adjacent teeth.

Figure 4B:
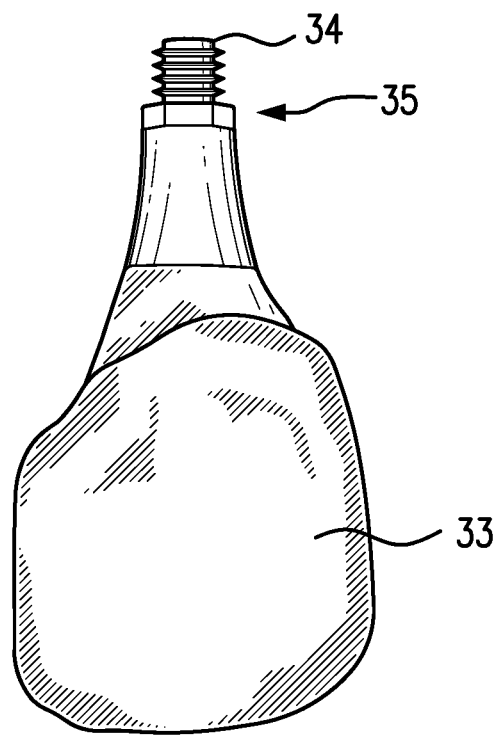
FIG. 4B illustrates a prosthetic tooth to be inserted into a dental implant.

After the dental implant has been implanted into a patient's jawbone and the implant mount has been removed, a prosthetic tooth is screwed into the top of the dental implant. FIG. 4B illustrates such a prosthetic tooth 33. The prosthetic tooth 33 has a threaded tip 34 and a hexagonal member 35 (with an external hexagon shape) like the proximal threaded tip 25 and proximal hexagonal member 24, respectively, of implant mount 19. Thus, the prosthetic tooth 33 mates with the dental implant 29 in the same way that the implant mount 19 mates with the dental implant 29. When the dental implant 29 is implanted into a patient's jawbone, it is important for the internal hexagon-shaped opening 31 of the dental implant 29 to have a specific rotational position with respect to the adjacent teeth. This is because the rotational position of the internal hexagon-shaped opening 31 determines the orientation of the prosthetic tooth in relation to the adjacent teeth. If the internal hexagon-shaped opening 31 does not have the proper rotational position, then the prosthetic tooth 33 that is screwed into the dental implant 29 will not have the proper orientation in the patient's mouth. Rather, it will be rotated to one side and will not line up properly with the adjacent teeth. There are ways to compensate for the internal hexagon-shaped opening 31 not having the proper rotational position, but much additional time and effort is needed to fabricate a prosthetic tooth that can be attached to the dental implant in the proper orientation.

One function of the internal hexagon-shaped opening 31 in the distal end of the dental implant 29 depicted in FIG. 3D and FIG. 4A is to lock the prosthetic tooth in place, since the tooth has an external hexagon-shaped member that fits into the internal hexagon-shaped opening of the dental implant. Although the embodiment of the dental implant depicted in FIG. 3D and FIG. 4A includes an internal hexagon-shaped opening, this opening could have other shapes, e.g., triangular or square-shaped. The important feature is for the dental implant to have a shape that mates with a similar shape on the prosthetic tooth and locks the tooth in place, so that unwanted rotation of the prosthetic tooth is prevented.

One conventional technique for trying to ensure that the internal hexagon-shaped opening in the dental implant has the proper rotational position is to place a vertical line on the implant mount and a vertical line on the surgical guide that line up with one another when the internal hexagon-shaped opening is in the proper rotational position. See, e.g., U.S. Pat. No. 8,414,296 B2 at column 9, lines 31-47. However, as noted above, this technique has several drawbacks. First, a visual inspection of both the implant mount and the surgical guide is necessary, which may be difficult, especially when the dental implant is to be implanted in the posterior of the mouth, and which also may depend too much on operator evaluation and experience. Second, the implant mount may be over-rotated in an effort to get the vertical lines or notches to line up, which may cause compression, warping and/or fracture of the surgical guide, and inaccurate placement of the implant in any of the three axes. A single surgical guide may have more than one guide tube and opening, and may be used to implant more than one implant. Compression or warping of the surgical guide caused by over-rotation of the implant mount can be an especially serious problem when the guide is needed to implant additional implants, since that procedure now must be done with a defective surgical guide.

The present invention overcomes these drawbacks. In one embodiment of the present invention, when the implant mount is being used to screw the dental implant into the patient's jawbone, the clutch teeth on the implant mount mate with corresponding clutch teeth on the guide tube of the surgical guide when the dental implant has been screwed the proper depth into the jawbone. These clutch teeth are disposed on the implant mount and guide tube in positions that ensure that, when the clutch teeth on the implant mount are fully mated with the clutch teeth on the guide tube, the internal hexagon-shaped opening of the dental implant will be in the proper rotational position and the dental implant will be at the proper depth. With the present invention, a visual inspection of vertical lines on the implant mount and surgical guide is not necessary. Rather, the tactile feedback provided by the clutch teeth fully mating with the clutch teeth on the guide tube informs the surgeon or dentist that the internal hexagon-shaped opening on the dental implant is in the proper rotational position and that the dental implant is at the proper depth.

It is important for the clutch teeth on the implant mount and the clutch teeth on the guide tube to fully mate with one another to get the internal hexagon-shaped opening in the dental implant in the proper rotational position. If the clutch teeth on the implant mount only partially mate with the clutch teeth on the guide tube, such that there is a gap between the clutch teeth on the implant mount and the clutch teeth on the guide tube, the internal hexagon-shaped opening in the dental implant will not be in the proper rotational position. For this reason, the clutch teeth should generally be short (i.e., the distance from the base to the tip of each tooth should be small).

If the clutch teeth on the implant mount do not fully mate with the clutch teeth on the guide tube when the dental implant is screwed in the first time (such that there is a gap between the clutch teeth on the implant mount and the clutch teeth on the guide tube), one technique for getting the clutch teeth on the implant mount to fully mate with the clutch teeth on the guide tube is to unscrew the dental implant a small amount, and then screw it back in again while placing gentle pressure on the top of the dental implant so that the dental implant is pushed more deeply into the jawbone. This technique can be repeated until the clutch teeth on the implant mount fully mate with the clutch teeth on the guide tube. Placing gentle pressure on the top of the dental implant is a technique commonly used by surgeons and dentists to get dental implants to screw in to the proper depth.

Another way to ensure that the clutch teeth on the implant mount fully mate with the clutch teeth on the guide tube is to have the clutch teeth be beveled, so that they mate with one another like the manner in which the blades of a pair of scissors mate. In this embodiment, the only portions of the beveled clutch teeth that mate with one another are the proximal ends of the clutch teeth on the implant mount, and the distal ends of the clutch teeth on the guide tube. This ensures that the clutch teeth on the implant mount can be rotated until they are fully mounted with the clutch teeth on the guide tube.

Yet another way to ensure that the clutch teeth on the implant mount fully mate with the clutch teeth on the guide tube is to place threads on the outer surface of the implant mount just proximal to the flange, and corresponding threads on the inner surface of the distal end of the guide tube. In this embodiment, the mating of the threads forces the implant mount to screw into the guide tube in a manner that ensures that the clutch teeth on the implant mount will fully mate with the clutch teeth on the guide tube. In this embodiment, it may be preferable to have the pitch of the threads on the outer surface of the implant mount and inner surface of the guide tube be the same as the pitch of the threads on the dental implant itself, so that the threads on the implant mount/guide tube are not trying to screw in the dental implant mount with one pitch, while the threads on the dental implant are trying to screw in the dental implant with a different pitch (i.e., so that the threads on the implant mount/guide tube do not "fight with" the threads on the dental implant). Accordingly, one may want to have implant mounts and guide tubes having threads with a variety of pitches, so as to match the variety of pitches of the threads on dental implants currently available.

Those skilled in the art will appreciate that indexing mechanisms other than clutch teeth may be included on the proximal surface of the flange of the implant mount and the distal surface of the guide tube. All that is necessary is that there be an indexing mechanism included on the proximal surface of the flange of the implant mount that mates with a corresponding indexing mechanism on the distal surface of the guide tube, and that causes the implant mount (and thus the dental implant) to stop rotating when the internal hexagon-shaped opening in the dental implant is in a specific rotational position with respect to the adjacent teeth.

Similarly, the indexing mechanisms need not be on the proximal surface of the flange of the implant mount and the distal surface of the guide tube. Rather, they can be in any two locations that mate with one another and thereby cause the dental implant to stop rotating when it is in a specific rotational position. For example, one indexing mechanism could be on the outside surface of the flange or the proximal shaft of the implant mount, and the other indexing mechanism could be on the outside or inside of the guide tube. Moreover, there need not be a guide tube in the surgical guide at all. Instead, one indexing mechanism (e.g., clutch teeth) could be on the flange of the implant mount (as shown in FIG. 3B, for example), while the other indexing mechanism could be on the distal surface of the surgical guide itself (e.g., molded into the thermoplastic or non-thermoplastic resinous base that the surgical guide is made from). Further, there need not be a separate piece referred to as an "implant mount." Rather, the "implant mount" could be part of the device used to screw the dental implant(s) into the jawbone (e.g., the hand-piece, ratchet device or drill), so that that one-piece device is used to screw the dental implant(s) into the jawbone. In that configuration, one indexing mechanism (e.g., clutch teeth) could be on the flange of the "implant mount" portion of the one-piece device, while the other indexing mechanism could be on the guide tube or molded directly into the surgical guide.

Figure 5A:
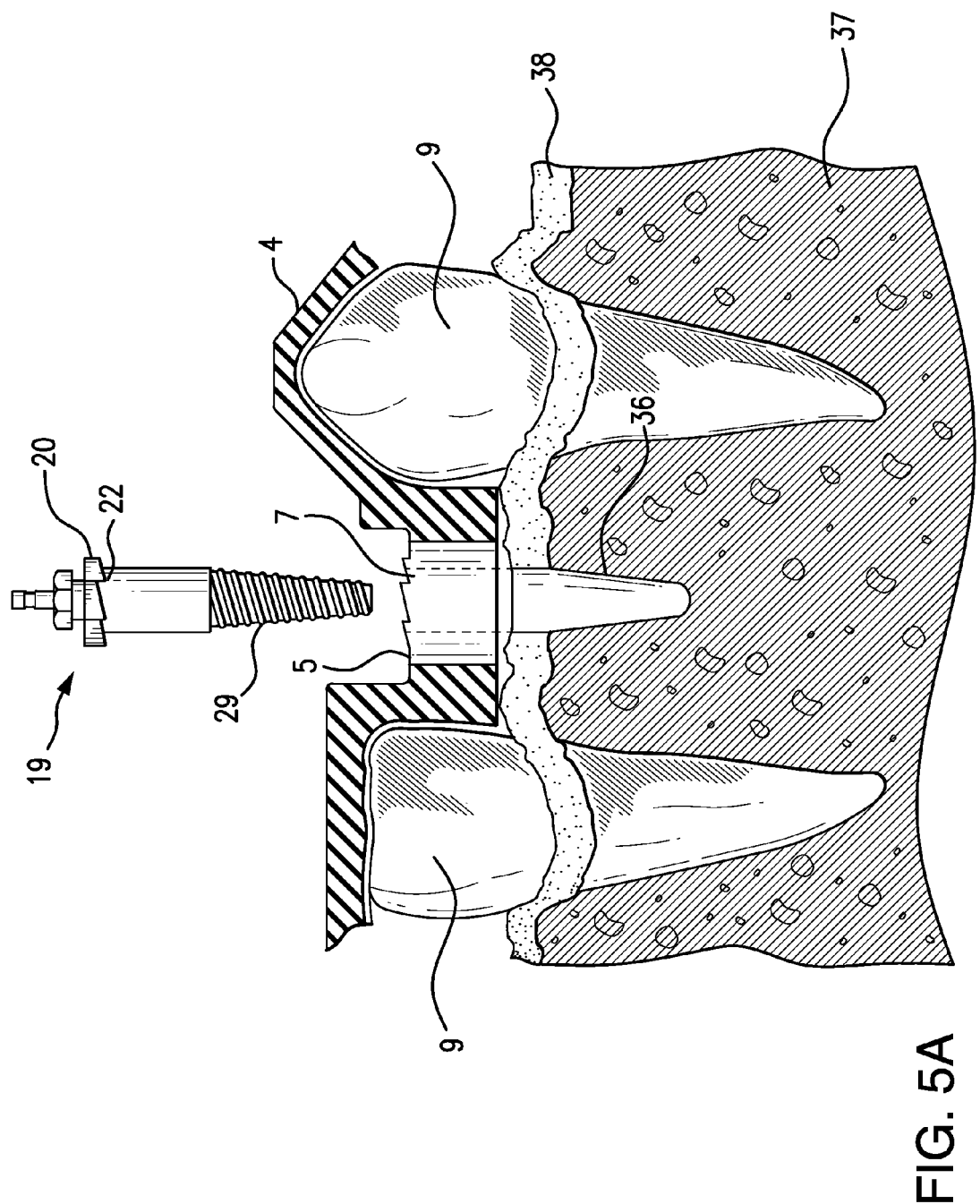
FIG. 5A illustrates an implant mount of the present invention attached to a dental implant about to be implanted in a patient's mouth using the surgical guide of the present invention.
Figure 5B:
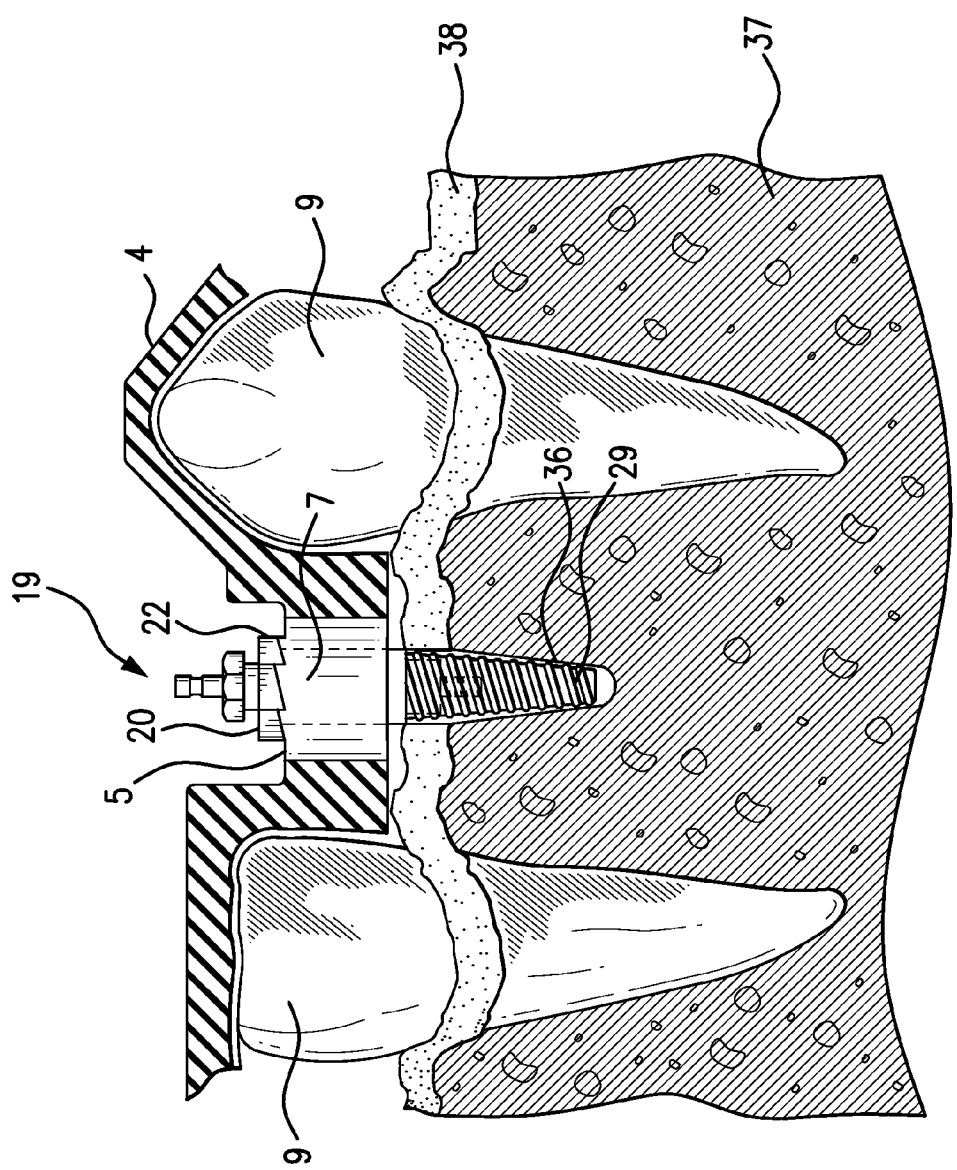
FIG. 5B illustrates an implant mount of the present invention attached to a dental implant that has been implanted in a patient's mouth using the surgical guide of the present invention.

FIGS. 5A and 5B show embodiments of the implant mount and guide tube of the present invention being used to implant a dental implant in a patient's jawbone. In FIG. 5A, the dental implant is only partly screwed into the previously-drilled hole 36 in the patient's jawbone 37 (which is covered by gums 38), which is shown by the fact that flange 20 with clutch teeth 22 of implant mount 19 has not yet come into contact with the distal end of the guide tube 5 with clutch teeth 7 of surgical guide 4. In FIG. 5B, the clutch teeth 22 of flange 20 have fully mated with the clutch teeth of the guide tube 5 of surgical guide 4. This ensures that the dental implant is screwed in to the proper depth in the patient's jawbone, and also ensures that the internal hexagon-shaped opening 31 in the dental implant 19 is in the proper rotational position with respect to the adjacent teeth.

As noted above, during the process of drilling a hole in the patient's jawbone into which a dental implant will be implanted, tube adapter sleeves of increasing diameter are dropped through the guide tube in the surgical guide. When using a surgical guide of the present invention, one may want to use tube adapter sleeves that have an indexing mechanism (like clutch teeth) that corresponds to the indexing mechanism on the distal surface of the guide tube of the surgical guide. This will prevent unwanted rotation of the tube adapter sleeves during the drilling process. However, it is not necessary that the tube adapter sleeves have such an indexing mechanism to be used with a surgical guide of the present invention. Rather, the tube adapter sleeves may just drop into the guide tube.

The embodiments of the surgical guide of the present invention depicted in the Figures described above include one guide tube and thus one opening through which a dental implant will be implanted. However, the surgical guide of the present invention may include multiple guide tubes and thus may be used to implant multiple dental implants. For example, the surgical guide of the present invention may be used with a patient having partial or fully edentulous arches, and who thus needs a full set of dental implants in one or both arches. As known to those skilled in the art, when a patient has a fully edentulous arch, the patient does not typically receive one implant for each missing tooth, with an individual prosthetic tooth being screwed onto each dental implant. Rather, when a patient has a fully edentulous arch, the patient receives approximately 6 to 8 dental implants in that arch (with a minimum of 4 implants in that arch), and then a prosthesis including a full arch of prosthetic teeth is attached to those dental implants. When a prosthesis including a full arch of prosthetic teeth is attached to dental implants in this manner, it is still important for the internal hexagon-shaped opening in the distal end of each dental implant to have the proper rotational position and depth. If the internal hexagon-shaped opening in the top of each dental implant does not have the proper rotational position and depth, then there will be ensuing difficulties in fabricating and attaching the prosthesis including a full arch of prosthetic teeth to the implants, which can only be overcome with significant additional time and effort.

When using the present invention, it is important for the guide tube to have the proper rotational position in the surgical guide, so that the clutch teeth on the guide tube are in the proper rotational position. This will ensure that the dental implant will be in the proper rotational position when the clutch teeth on the implant mount fully mate with the clutch teeth on the guide tube. One way of ensuring that the guide tube is in the proper rotational positional position within the surgical guide is as follows.

As described above, the surgical guide and protocol are often prepared by a dental implant manufacturer, a supplier of dental implant case planning software, or a dental laboratory. Using CT (CBCT-DICOM files) data and optical scan (STL files-STereoLithography) data regarding the precise location of the teeth, gums and bone in the patient's mouth, a surgical guide designed specifically for the patient's mouth may be designed virtually, and then may be manufactured using a printing or milling process. When designing a surgical guide virtually and using the present invention to ensure that the dental implants are in the proper rotational position and depth, the desired rotational position of the internal hexagon-shaped opening on the dental implants should be established during the virtual design process. The desired rotational position of the internal hexagon-shaped opening is the one that will ensure that the prosthetic teeth attached to the dental implants will be in the proper orientation when they are screwed into the dental implants. Once the desired rotational position of the internal hexagon-shaped opening is established virtually, then the rotational position of the guide tube that will result in that desired rotational position of the internal hexagon-shaped opening should be determined, also as part of the virtual design process. Finally, the opening in the surgical guide should be designed in such a way that the guide tube can only fit into the opening when it is in its proper rotational position within the guide tube. For example, as described above, the outer surface of the guide tube may have a certain shape (e.g., hexagonal or square-shaped), and the internal surface of the opening in the guide tube may have the corresponding shape. In other words, with the present invention, part of the virtual design of the surgical guide is having an opening that is specifically designed to receive the guide tube only when it is in the proper rotational position within the surgical guide. Once the surgical guide has been virtually designed, including having an opening that is specifically designed to receive the guide tube only when it is in the proper rotational position within the surgical guide, it may be printed or milled using processes familiar to those skilled in the art.

Making a virtual determination of the proper rotational position of the internal hexagon-shaped opening on the dental implants may be useful even when a surgical guide is not utilized. For example, there has been experimentation with implanting dental implants into the jawbone of a patient without a surgical guide, with a virtual image of the dental implant and the patient's mouth being displayed on a computer screen in the operating room using GPS coordinates for the dental implant and the relevant features of the patient's mouth. With this technology, it will continue to be important to have the internal hexagon-shaped opening on the dental implant be in the proper rotational position. For this reason, it will be important to determine that rotational position virtually before the implants are implanted, and then use that information during the implantation of the implants to make sure that the implants are screwed into the jawbone in such a way that the internal hexagon-shaped opening on the dental implant is in the proper rotational position. One method of achieving this would be to have a computer (e.g., a computer linked to the computer screen in the operating room referred to above) produce a visual or audio signal when the implant is screwed into the jawbone in such a way that the internal hexagon-shaped opening on the dental implant is in the proper rotational position.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

The invention claimed is:

1. A system for ensuring that a dental implant is screwed in to a proper rotational position and depth when it is implanted into a jawbone of a patient comprising:
   an implant mount configured to be removably attached to the dental implant, wherein the implant mount comprises a first indexing mechanism comprising clutch teeth; and
   a surgical guide comprising at least one guide tube, wherein the guide tube comprises a second indexing mechanism comprising clutch teeth;
   wherein the first indexing mechanism is configured to mate with the second indexing mechanism when the implant mount is used to screw the dental implant into a jawbone of a patient;
   wherein the clutch teeth of the first indexing mechanism each have a base and a tip with a sloped surface extending from the base to the tip, and are formed adjacent to one another;
   wherein the clutch teeth of the second indexing mechanism each have a base and a tip with a sloped surface extending from the base to the tip, and are formed adjacent to one another; and
   wherein the clutch teeth of the first indexing mechanism and the clutch teeth of the second indexing mechanism have corresponding shapes so that they can fully mate with each other.

2. The system of claim 1 wherein the implant mount has a flange comprising a proximal surface, and the clutch teeth are located on the proximal surface of the flange.

3. The system of claim 1 wherein the guide tube has a distal surface, and the clutch teeth are located on the distal surface.

4. The system of claim 1 wherein the first indexing mechanism and the second indexing mechanism are configured so that when they fully mate with one another, the dental implant will be screwed in to the proper rotational position and depth in the patient's jawbone.

5. The system of claim 1, wherein the guide tube comprising clutch teeth is permanently affixed to the surgical guide.

6. The system of claim 1, wherein the surgical guide and guide tube are closed on all sides.

7. A device configured to assist with ensuring that a dental implant is screwed in to a proper rotational position and depth when it is implanted into a jawbone of a patient comprising:
   an implant mount comprising a first indexing mechanism comprising clutch teeth that is configured to mate with a second indexing mechanism comprising clutch teeth on a guide tube of a surgical guide;
   wherein the clutch teeth of the first indexing mechanism each have a base and a tip with a sloped surface extending from the base to the tip, and are formed adjacent to one another; and
   wherein the clutch teeth of the first indexing mechanism have a shape corresponding to the shape of the clutch teeth of the second indexing mechanism so that they can fully mate with the clutch teeth of the second indexing mechanism.

8. The device of claim 7 wherein the implant mount has a flange with a proximal surface, and the indexing mechanism on the implant mount is located on the proximal surface.

9. The device of claim 7 wherein the first indexing mechanism is configured such that when it fully mates with the second indexing mechanism, the dental implant will be screwed in to the proper rotational position and depth in the patient's jawbone.

10. A device configured to assist with ensuring that a dental implant is screwed in to a proper rotational position and depth when it is implanted into a jawbone of a patient comprising:
    a surgical guide comprising at least one guide tube, wherein the guide tube comprises a second indexing mechanism comprising clutch teeth that is configured to mate with a first indexing mechanism comprising clutch teeth on an implant mount;
    wherein the clutch teeth of the second indexing mechanism each have a base and a tip with a sloped surface extending from the base to the tip, and are formed adjacent to one another; and
    wherein the clutch teeth of the second indexing mechanism have a shape corresponding to the shape of the clutch teeth of the first indexing mechanism so that they can fully mate with the clutch teeth of the first indexing mechanism.

11. The device of claim 10 wherein the guide tube has a distal surface, and the second indexing mechanism is located on the distal surface.

12. The device of claim 10 wherein the second indexing mechanism is configured such that when it fully mates with the first indexing mechanism, the dental implant will be screwed in to the proper rotational position and depth in the patient's jawbone.

13. The device of claim 10, wherein the guide tube comprising clutch teeth is permanently affixed to the surgical guide.

14. The device of claim 10, wherein the surgical guide and guide tube are closed on all sides.

15. A method of ensuring that a dental implant is screwed in to a proper rotational position and depth when it is implanted into a jawbone of a patient comprising:
    placing a surgical guide having a guide tube in a patient's mouth so that the guide tube is aligned with a location in the jawbone where a dental implant is to be implanted, wherein the guide tube comprises a second indexing mechanism comprising clutch teeth;
    removably attaching an implant mount to the dental implant, wherein the implant mount comprises a first indexing mechanism comprising clutch teeth;
    disposing the attached implant mount and dental implant through the guide tube; and rotating the attached implant mount and dental implant so as to screw the dental implant into the patient's jawbone until the first indexing mechanism mates with the second indexing mechanism;

wherein the clutch teeth of the first indexing mechanism each have a base and a tip with a sloped surface extending from the base to the tip, and are formed adjacent to one another;

wherein the clutch teeth of the second indexing mechanism each have a base and a tip with a sloped surface extending from the base to the tip, and are formed adjacent to one another; and wherein the clutch teeth of the first indexing mechanism and the clutch teeth of the second indexing mechanism have corresponding shapes so that they can fully mate with each other.

16. The method of claim 15 wherein the guide tube has a distal surface, and the clutch teeth are located on the distal surface.

17. The method of claim 15 wherein the implant mount has a flange comprising a proximal surface, and the clutch teeth are located on the proximal surface.

18. The method of claim 15 wherein the first indexing mechanism and the second indexing mechanism are configured so that when the first indexing mechanism fully mates with the second indexing mechanism, the dental implant will be screwed in to the proper rotational position and depth in the patient's jawbone.

19. The method of claim 15, wherein the guide tube comprising clutch teeth is permanently affixed to the surgical guide.

20. The method of claim 15, wherein the surgical guide and guide tube are closed on all sides.

* * * * *